(12) United States Patent
Bascle et al.

(10) Patent No.: US 7,346,385 B2
(45) Date of Patent: Mar. 18, 2008

(54) METHOD AND APPARATUS FOR NEEDLE PLACEMENT AND ENTRY POINT DETERMINATION IN PERCUTANEOUS PROCEDURES

(75) Inventors: Benedicte Bascle, Plainsboro, NJ (US); Nassir Navab, Plainsboro, NJ (US); Bernhard Geiger, Plainsboro, NJ (US)

(73) Assignee: Siemens Corporate Research, Inc., Princeton, NJ (US)

( * ) Notice: Subject to any disclaimer, the term of this patent is extended or adjusted under 35 U.S.C. 154(b) by 639 days.

(21) Appl. No.: 10/683,650

(22) Filed: Oct. 10, 2003

(65) Prior Publication Data

US 2004/0078045 A1 Apr. 22, 2004

Related U.S. Application Data

(62) Division of application No. 09/883,422, filed on Jun. 18, 2001, now abandoned.

(60) Provisional application No. 60/212,199, filed on Jun. 16, 2000.

(51) Int. Cl.
*A61B 19/00* (2006.01)
(52) U.S. Cl. ........................ 600/424; 606/130
(58) Field of Classification Search ............... 606/130; 128/898; 600/566, 424
See application file for complete search history.

(56) References Cited

U.S. PATENT DOCUMENTS 5,799,055 A * 8/1998 Peshkin et al. ............... 378/42

* cited by examiner

*Primary Examiner*—Michael Thaler (57) ABSTRACT

A method for determining the best entry point for a percutaneous procedure, such as with a biopsy needle, comprises selecting first and second arbitrary entry points on a patient; determining the three dimensional (3-D) orientation of the needle at the first arbitrary entry point for pointing the needle at the primary target; determining the 3-D orientation of the needle at the first arbitrary entry point for pointing the needle at the secondary target; determining the 3-D dimensional orientation of the needle at the second arbitrary entry point for pointing the needle at the primary target; determining the 3-D orientation of the needle at the second arbitrary entry point for pointing the needle at the secondary target; determining a 3-D line representing the intersection of a first plane containing the first arbitrary entry point, the primary target point, and the secondary target point, and a second plane containing the second arbitrary entry point, the primary target, and the secondary target point, whereby the 3-D line provides a position and orientation for the needle for performing needle biopsy of the primary target through the secondary target.

6 Claims, 7 Drawing Sheets

Fig. 1: Needle Placement by visual Servoing in 3 Successive Planes using 2 views Figure 2 - Visual Servoing of a Needle in a plane using cross-ratios Fig. 3 Needle orientation from fixed point F to multiple targets (a) arbitrary planes P1 and P2 (b) (c) (d) visual servoing to T of needle rotating in P1 defines lines D1. (e) visual servoing in P2 defines D2. D1 and D2 give viewing plane $\Pi_{FT}$ Similar approach gives $\Pi_{FU}$ (f) visual servoing in second image plane of needle rotating in $\Pi_{FT}$ The resulting orientation of the needle is along (FT). Similar approach to be applied for $\Pi_{FU}$ Fig 4 Best entry point to reach one target by passing through secondary target It can be found by first orienting the needle to the targets from 2 arbitrary entry points

Figure 7. Method for visual servoing of a needle in a plane in a fixed number of iterations. This approach is used in the previous approaches.

METHOD AND APPARATUS FOR NEEDLE PLACEMENT AND ENTRY POINT DETERMINATION IN PERCUTANEOUS PROCEDURES

This application is a divisional application of Ser. No. 09/883,422, filed Jun. 18, 2001.

The present invention relates to the field of percutaneous procedures and, more specifically, to method and apparatus for needle placement, such as for needle biopsy, and for determining an appropriate entry point for such a needle.

Reference is hereby made to copending Provisional Application No. 60/212,199 filed on Jun. 16, 2000 in the names of Benedicte Bascle, Nassir Navab, and Bernhard Geiger and entitled "METHOD FOR NEEDLE PLACEMENT IN A FIXED NUMBER OF ITERATIONS USING PERSPECTIVE INVARIANTS AND METHOD FOR DETERMINING THE BEST ENTRY POINT FOR PERCUTANEOUS PROCEDURES", whereof the disclosure is herein incorporated by reference.

Reference is also herein made to the following documents whereof the disclosure is herein incorporated by reference: U.S. Pat. No. 6,028,912 "APPARATUS AND METHOD FOR POINT RECONSTRUCTION AND METRIC MEASUREMENT ON RADIOGRAPHIC IMAGES"; U.S. Pat. No. 5,930,329 "APPARATUS AND METHOD FOR DETECTION AND LOCALIZATION OF A BIOPSY NEEDLE OR SIMILAR SURGICAL TOOL IN A RADIOGRAPHIC IMAGE"; and pending U.S. patent application Ser. No. 09/408,929, entitled "METHOD AND APPARATUS FOR VISUAL SERVOING OF A LINEAR APPARATUS" and filed on 30 Sep. 1999 in the name of inventor Benedicte Bascle.

In accordance with an aspect of the present invention, a method is provided for determining the best entry point for percutaneous procedures, given a primary target for the biopsy and a secondary target through which the needle must pass on its way to the primary target.

In accordance with another aspect of the invention, a method is provided for positioning a biopsy needle from a given entry point to a given target.

In accordance with another aspect of the invention, a method is provided for visual servoing of a needle in a plane in a fixed number of iterations.

In accordance with an aspect of the present inventive concepts, it is herein shown how precise 3D-alignment of a tool from a fixed entry point to a target can be achieved by performing visual servoing of the tool in 3 successive planes using two different views. Visual servoing of the needle or tool in each plane is achieved using a technique based on projective invariants. 3D alignment is obtained in exactly twelve iterations using the technique. If there are multiple (n) targets, the approach does not require n*12 iterations, but 6*(n+1).

In accordance with another aspect of the present inventive concepts, a method for finding the entry point to reach a given target while passing through a secondary target is herein described.

The invention will be more fully understood from the following detailed description, in conjunction with the Drawing, in which.

With regard to needle placement by visual servoing in 3 successive planes, using 2 views, reference is made to copending U.S. patent application No. 08/722,725, entitled "APPARATUS AND METHOD FOR POSITIONING A BIOPSY NEEDLE" and filed 30 Sep. 1996 in the name of inventors Nassir Navab and Bernhard Geiger, whereof the disclosure is herein incorporated by reference.

Figure 1:
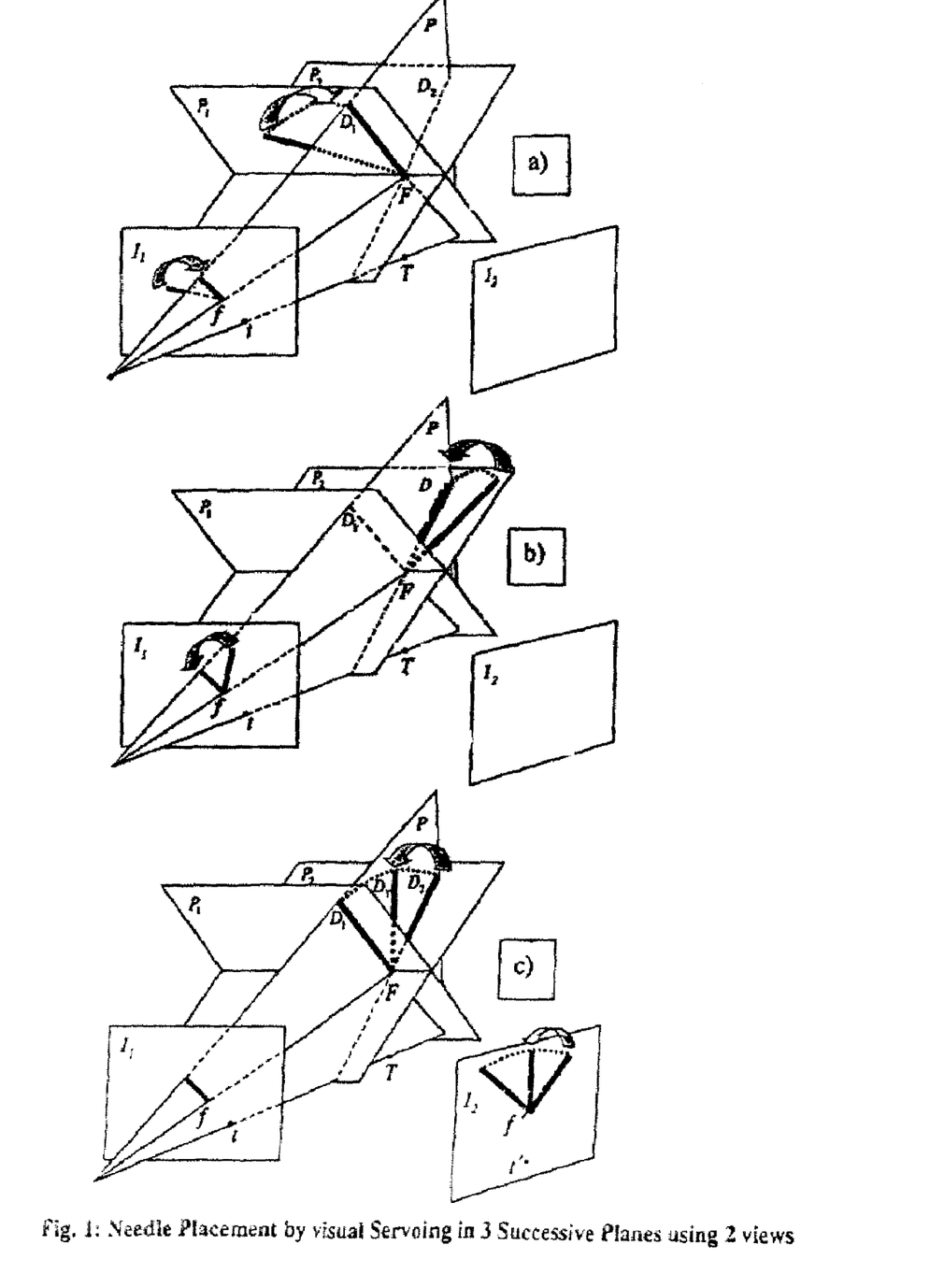
FIG. 1 shows needle placement by visual servoing in 3 successive planes using 2 views.

Reference now is made to FIG. 1

For illustrative purposes, it is assumed that imaging is provided by a simple uniplanar X-ray fluoroscope (C-arm) or any other imaging modality whose imaging process can be modeled by a pinhole camera model. The needle itself is manipulated by a mechanical device such as a passive or active robotic arm that allows arbitrary pivoting of the needle around its tip. The operator, physician, surgeon or doctor, chooses a fixed needle entry point F on the patient, and places the needle device in a way that its needle tip is located at that entry point. No calibration of the set-up or registration of the patient to the set-up is required.

The C-arm is then positioned so that the target area and a part of the needle are both visible on the X-ray image $I_1$. The surgeon defines the projection f of the needle entry pointy F and projection t of the 3D anatomical target T in the image. At this point of the description, it is assumed T remains static during the procedure.

First, the mechanical device moves the needle in an arbitrary plane $P_1$ containing F until the projection of the needle is aligned with the target t in the image $I_1$ (see FIG. 1a). This can be performed in 3 iterations using the visual servoing technique presented in the next section. The final position of the needle in plane P.sub.1 is called $D_1$.

The system repeats this process by choosing a second plane $P_2$ containing F. The choice of $P_2$ is arbitrary. in practice, the system takes $P_2$ perpendicular to $P_1$ for precision purposes. The needle is rotated in plane $P_2$ until it is visually aligned to the target t in the image $I_1$ (see FIG. 1b). This is done as previously described by using the visual servoing technique presented in section 2. The position of the needle that gives visual alignment is called Th $D_2$.

The positions of the needle $D_1 \subset P_1$ and $D_2 \subset P_2$ define a unique plane P, which contains the X-ray source, the target point T and the fixed entry point F. This is essentially the maximum information that can be obtained from a single viewpoint.

The physician needs to move the C-arm to a second viewing direction. The surgeon defines projection F' of needle entry point F and the projection t' of the 3D target point T in the new image $I_2$. Next, the needle is moved only in the plane P until the needle is once again visually aligned to the target in the image $I_2$ (see FIG. 1c). This is done using the visual servoing approach of section 2. This results in the final 3D alignment $D_T$ of the needle, the entry point and the anatomic target point. The needle is then ready to be inserted. The correctness of the alignment can also be checked by moving the C-arm to a third viewing direction.

VISUAL SERVOING OF A NEEDLE IN A PLANE USING CROSS-RATIOS

With regard to visual servoing of a needle in a plane using cross-ratios, reference is made to the afore-mentioned U.S. patent application Ser. No. 09/408,929, entitled "METHOD AND APPARATUS FOR VISUAL SERVOING OF A LINEAR APPARATUS".

Figure 2:
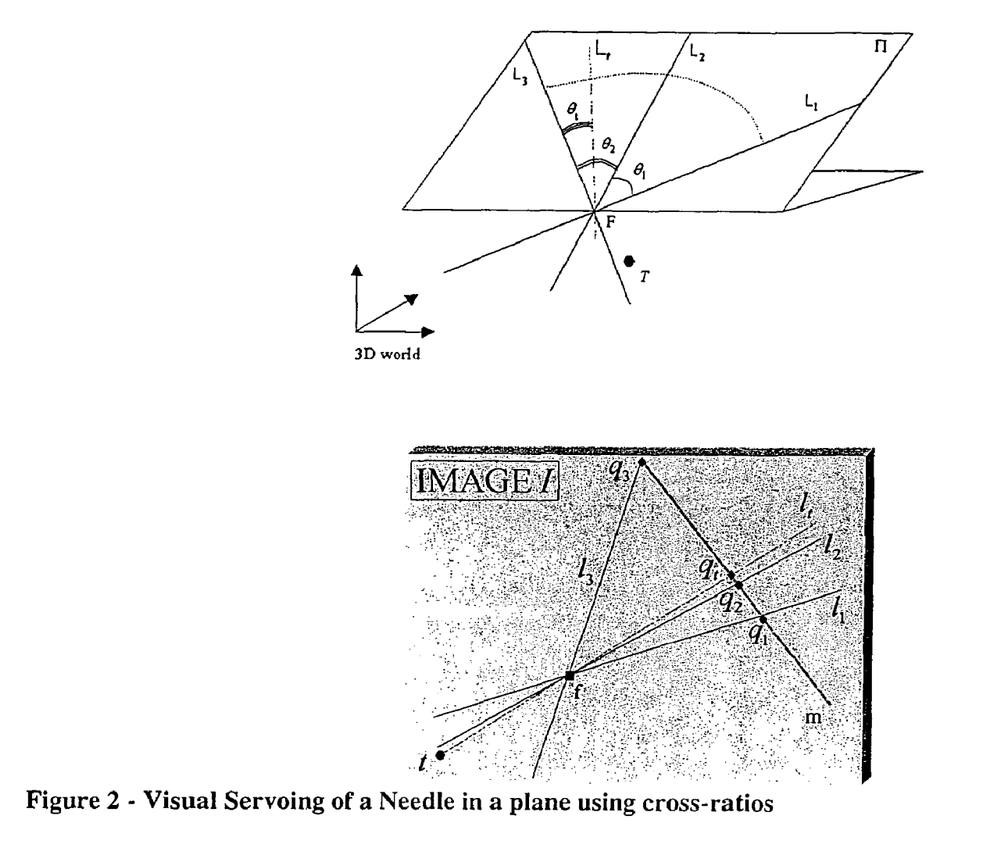
FIG. 2 shows visual servoing of a needle in a plane using cross-ratios.

In the previous section, it was shown how 3D alignment of a needle to a target can be achieved by performing visual servoing of the needle in three successive planes. There now follows an explanation of how the visual servoing of the needle in a plane is performed. This is a new technique based on projective invariants and is described as follows:

Reference now is made to FIG. 2.

Let $\Pi$ be the plane in which the needle is rotated, and F the fixed point around which the rotation is done. The initial orientation $L_1$ of the needle in plane $\Pi$ is arbitrary. T is the 3D target point.

An image I is taken of the scene. The 3D position $L_1$ of the needle projects onto line $l_1$ in the image. The position of $l_1$ is detected and stored in memory.

The needle is rotated in plane $\Pi$ around fixed point F by an arbitrary amount $\theta_1$. This brings it to position $L_2$. Another image is taken. The 3D line $L_2$ projects onto 2D line $l_2$ in the image. The position of $l_2$ is detected and stored in memory.

The needle is rotated again by an angle $\theta_2$. This puts it into $L_3$. Another image is obtained. $l_3$ projects onto $l_3$ in the image. $L_3$ is detected and its position stored in memory.

The intersection point of $l_1$, $l_2$ and $l_3$ denoted f, is determined by least squares. Note that f is the projection of the fixed point F around which the needle is rotated.

Let t be the projection of the 3D target T in the image. We assume t remains static during the procedure. The position of t is given interactively by the surgeon.

The line $l_t$=(ft)is constructed. Note that $l_t$ is the 2D projection of the 3D position $L_t$ of the needle that achieves visual servoing (e.g. the visual alignment of the needle and the target) and that we wish to estimate.

$l_1$, $l_2$, $l_3$ and $l_t$ form a pencil of 2D lines. The cross-ratio c=$(l_1, l_2, l_3, l_t)$ of these lines is calculated. This is done using an arbitrary line m that intersects all four lines. If $q_1=l_1 \cap m$, $q_2=l_2 \cap m$, $q_3=l_3 \cap m$ and $q_t=l_t \cap m$ are the intersections of $l_1$, $l_2$, $l_3$, $l_t$ with m, then $$c=(l_1,\ l_2,\ l_3,\ l_t)=(q_1,\ q_2,\ q_3,\ q_t)=(q_1 q_3\ {}^*q_2 q_t) \div (q_1 q_t\ {}^* q_2 q_3).$$

Note that the value of c is invariant to the choice of the line m.

Cross-ratios are one of the invariants of projective geometry. Therefore the cross-ratio of a pencil of 3D lines is equal to the cross-ratio of the pencil of 2D lines formed by its perspective projections in an image. Therefore the cross-ratio $(L_1, L_2, L_3, L_t)$ of the four 3D lines $L_1, L_2, L_3$ and $L_t$ is equal to c, eg. $(L_1, L_2, L_3, L_t)=(l_1, l_2, l_3, l_t)=c$.

From $(L_1, L_2, L_3, L_t)$, we estimate the angle $\theta_t$ necessary to rotate the needle from position $L_3$ to $L_t$. The formula for $\theta_t$ comes from the relationship between the cross-ratio of four lines and the angle between these lines. This gives:

$$(L_1, L_2, L_3, L_t) = \frac{(\sin(\theta_1 + \theta_2) * \sin(\theta_2 + \theta_t))}{(\sin(\theta_1 + \theta_2 + \theta_t) * \sin\theta_2)}.$$

Using the fact that $(L_1, L_2, L_3, L_t)$=c, the equation can be rewritten as follows:

$$(c-1)\sin\theta_2 \cos\theta_t + \left(\frac{c\sin\theta_2}{\tan(\theta_1 + \theta_2)} - \cos\theta_2\right)\sin\theta_t = 0.$$

This equation in $\theta_t$ is solved using the change of variable g=$\tan^{\theta_{t/2}}$. Note that there are in general 2 solutions to this equation. However, these solutions are equal modulo $\pi$, so that they define the same line $L_t$.

The needle is rotated by angle $\theta_t$ from position $L_3$ to $L_t$. This achieves visual servoing. At position $L_t$ the needle is visually aligned to the target in the 2D image.

Note that only visual alignment is achieved. Unless the 3D target T belongs to plane $\Pi$, full 3D alignment is not achieved. As shown in section 1, complete 3D alignment can be obtained only by performing visual servoing of the needle in several successive planes.

It should be noted that this visual servoing technique does not require any camera calibration. It also converges in exactly three iterations, contrary to most visual servoing approaches, which require a variable and typically a larger number of iterations. This is important in X-ray applications where each new image increases the radiation exposure of both patient and surgeon.

This visual servoing approach can be applied to any imaging device that can be approximated by a pinhole camera. In applications where the number of iterations is not critical, precision can be improved by considering n>3 successive needle positions $L_1, L_2, \ldots, L_n$. Then $\theta_t$ can then be estimated by least-square approximation from all the possible cross-ratios between lines $L_1, L_2, \ldots, L_n$.

In accordance with the present inventive concepts, combining both approaches (see section 1 and 2) ensures that 3D needle placement can be achieved in a fixed number (12) of iterations. This is very important as this limits the radiation exposure of both surgeon and patient and is an advantage of the present method over prior art methods, which usually cannot guarantee the number of iterations that they will need to converge.

If there are several targets to align the needle to, the alignment to all n targets can be performed in 6*(n+1) iterations, instead of 12*n iterations, since some of the steps of the alignment can be used for several targets. The variation for orientation of a needle from a fixed point to multiple targets by visual servoing is the following:

It is herein assumed for the purpose of illustrative example that imaging is provided by a simple uniplanar X-ray fluoroscope (C-arm) or another imaging modality that can be approximated by a pinhole camera model. The needle itself is manipulated by a mechanical device such as a passive or active robotic arm that allows arbitrary pivoting of the needle around its tip. The surgeon chooses a fixed needle entry point F on the patient, and places the needle device in such a way that its tip is located at that entry point. No calibration of the set-up or registration of the patient to the set-up is required.

The C-arm or imaging modality is then positioned, so that the target area and a part of the needle are both visible on the image. This position corresponds to the first image plane.

The surgeon defines the projection t of the 3D anatomical target T in the image. At this point of the description, it is assumed T remains static during the procedure. Other target points can be defined as necessary. To simplify the description of the approach and the figures, the case of 2 targets T and U is considered; however, this is not intended to be limiting as the approach applies to n targets.

Figure 3:
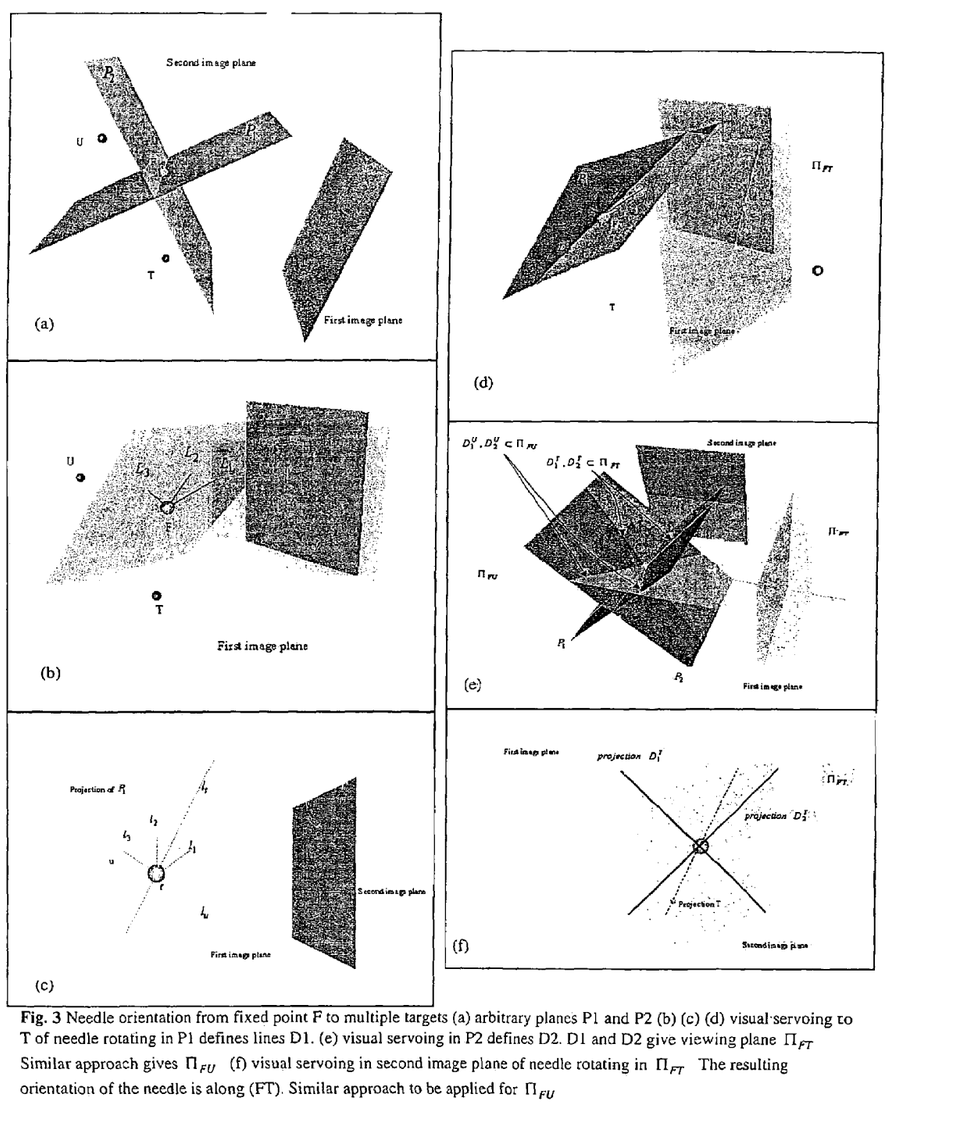
FIG. 3 shows needle orientation from fixed point F to multiple targets.

Let $P_1$ and $P_2$ be two arbitrary and non-parallel planes containing F (see FIG. 3a). For details on the choice of $P_1$ and $P_2$, see discussion below.

The mechanical device (passive mechanical arm or active robot) first places the needle in plane $P_1$ at an arbitrary position $L_1 \subset P_1$ (see FIG. 3b). An image is taken. 3D line $L_1$ projects onto 2D image (see FIG. 3c). Then the needle is rotated in plane $P_1$ by an arbitrary angle $\theta_1$. This brings it to position $L_2$, which project onto 2D position $l_2$ in a new image. The needle is again rotated, this time by an amount $\theta_2$. This puts it into position $L_3$. Another image is obtained and the corresponding 2D line $l_3$ is measured. The intersection point of all $l_1$, $l_2$ and $l_3$, denoted f, is determined by least squares. Note that f is the projection of the fixed point F around which the needle is rotated.

Let t and u be the 2D projections of the 3D targets T and U in the X-ray image. They are given interactively by the surgeon.

Let us consider t first. The line $l_t=(ft)$ is constructed. Note that $l_1$ is the 2D projection of a 3D line $L_t$ in plane $P_1$. The rotation angle between $L_3$ and $L_t$ is denoted $\theta_t$. First we calculate the cross-ratio $c=(l_1, l_2, l_3, l_t)$ of the 4 intersecting 2D lines. This can be done using an arbitrary line m that intersects all four lines. If $$q_1=l_1 \cap m,\ q_2=l_2 \cap m,\ q_3=l_3 \cap m,\ q_t=l_t \cap m,$$

then $$c=(q_1 q_3 * q_2 q_t) \div (q_1 q_t * q_2 q_3).$$

Note that the value of c is invariant to the choice of the line m. Since cross-ratios are one of the invariants of projective geometry, we have the following equation: $(L_1, L_2, L_3, L_t)=(l_1, l_2, l_3, l_t)=c$. And from the relationship between cross-ratios and angles, we can write the following formula:

$$(L_1, L_2, L_3, L_t) = \frac{(\sin(\theta_1 + \theta_2) * \sin(\theta_2 + \theta_t))}{(\sin(\theta_1 + \theta_2 + \theta_t) * \sin\theta_2)}.$$

Therefore, we can deduce the angle $\theta_t$ from the value of c measured in the image by using the following equation:

$$(c-1)\sin\theta_2 \cos\theta_t + \left(\frac{c\sin\theta_2}{\tan(\theta_1 + \theta_2)} - \cos\theta_2\right)\sin\theta_t = 0.$$

There are in general 2 solutions to this equation. However, these solutions are equal modulo $\pi$, so that they define the same line $L_t$. The needle is rotated by angle $\theta_t$ from position $L_3$ to $L_t$ (see FIG. 3d). This achieves visual servoing of the needle in plane $P_1$, e.g. the visual alignment of the needle and the target T. In the reminder of this paper, $L_t$ will be called $D_1^T$ (see FIG. 3e). Note that the 3D alignment of the needle to T is not achieved yet.

Similarly, the line $l_u=(fu)$ can be constructed and the rotation angle $\theta_u$ that achieves visual servoing of the needle to target U can be deduced from the cross-ratio $(l_1, l_2, l_3, l_u)$.

The resulting position of the needle in plane $P_1$ is noted $D_1^u$ (see FIG. 3e). Note that the same lines $l_1$, $l_2$, $l_3$ are used to achieve visual servoing in plane $P_1$ for all the targets.

The same visual servoing procedure can be applied in plane $P_2$ for each target. This defines 2 lines $D_2^T$ and $D_2^U$ belonging to plane $P_2$ and visually aligned to the targets T and U in the image defined by the first position of the X-ray C-arm (see FIG. 3e).

Let $\Pi_{FT}=D_1^T \wedge D_2^T$ be the plane defined by 3D lines $D_1^T$ and $D_2^T$. Since both lines project to (ft) in the image plane, this plane contains F, T and the center of the camera corresponding to the first position of the X-ray source. We call this plane the viewing plane of target T and entry point F for the first image plane (see FIG. 3e). This is the maximum information we can get about T from a single viewpoint. Similarly, $\Pi_{FU}=D_1^U \wedge D_2^U$ is the viewing plane of target U and entry point F for the first image plane.

At this point, the physician needs to move the C-arm to a second viewing direction. The surgeon also needs to define the 2D projections t' and u' of the 3D target points T and U in the new X-ray image.

Then we find the position of the needle in plane $\Pi_{FT}$ that is visually aligned to target T in the new image (see FIG. 3f). This can be done by moving the needle first to $D_1^T$, then to $D_2^T$, then rotating it to a third arbitrary position and applying our cross-ratio based approach for visual servoing of the needle in a plane (see details above). This results in the complete 3D alignment of the needle, entry point F and target point T. The needle is then ready to insert to reach target T. The correctness of the alignment can also be checked by moving the C-arm to a third viewing direction.

Similarly, the 3D orientation of the needle (FU) can be determined by moving the needle in plane $\Pi_{FU}$ and visually aligning it to target U in the image.

Note that the complete orientation of the needle from one fixed point to one target only takes 12 iterations (or X-ray images). However, as described above, if there are n targets, we do not need to do the complete needle orientation procedure for each target. Careful step counting shows that only 6*(n+1) iterations are needed to determine the 3D orientations of the needle.

Note that this visual servoing technique does not require any camera calibration. In addition and contrary to most visual servoing approaches that usually require a variable and often large number of iterations, it converges in a fixed number of iterations. This is important in X-ray applications where each new image increases the radiation exposure to both patient and surgeon.

After 3D alignment of the needle, the insertion depth required to reach the target from the entry point can be estimated using cross-ratios. For this, we use markers mounted on the needle guide at known intervals. The cross-ratio of the position of these markers, the entry point and the target is measured in the image. Since cross-ratios are projective invariants, the 3D distance from the entry point to the target can be deduced from the cross-ratio.

Visual servoing in a plane is most precise if the plane is parallel to the image plane. Therefore ideally $P_1$ and $P_2$ should be parallel to the image plane. However, for a line $D_1^T$ in plane $P_1$ and a line $D_2^T$ in plane $P_2$ to define a plane with good precision, $P_1$ and $P_2$ should ideally be perpendicular. The compromise we found is to use perpendicular planes $P_1$ and $P_2$ which are tilted forty-five degrees with respect to the image plane. The error analysis simulations shown in the paragraph below seem to support this choice.

The visual servoing approach in accordance with the principles of the invention can be applied to any imaging device that can be approximated by a pinhole camera. In applications where the number of iterations is not critical, the precision of visual servoing in a plane can be improved by considering n>3 successive needle positions $L_1$, $L_2, \ldots, L_n$. Then $\theta_t$ can then be estimated by least-square approximation from all the possible cross-ratios between lines $L_1, L_2, \ldots, L_n$. Similarly, if more than two positions of the imaging device are used, then the viewing planes $\Pi_{FT}$ of the target T and entry point F corresponding to each camera pose can be intersected by least-squares in order to determine the 3D orientation (FT). Using more camera positions increases precision.

The following part relating to a method for finding the best entry point for percutaneous procedures is distinct from the foregoing material and it applies to any imaging modality and any method for aligning a needle or linear tool to a target from a given entry point on the patient. It can be combined with the methods presented in section 1 and 2, or others.

Figure 4:
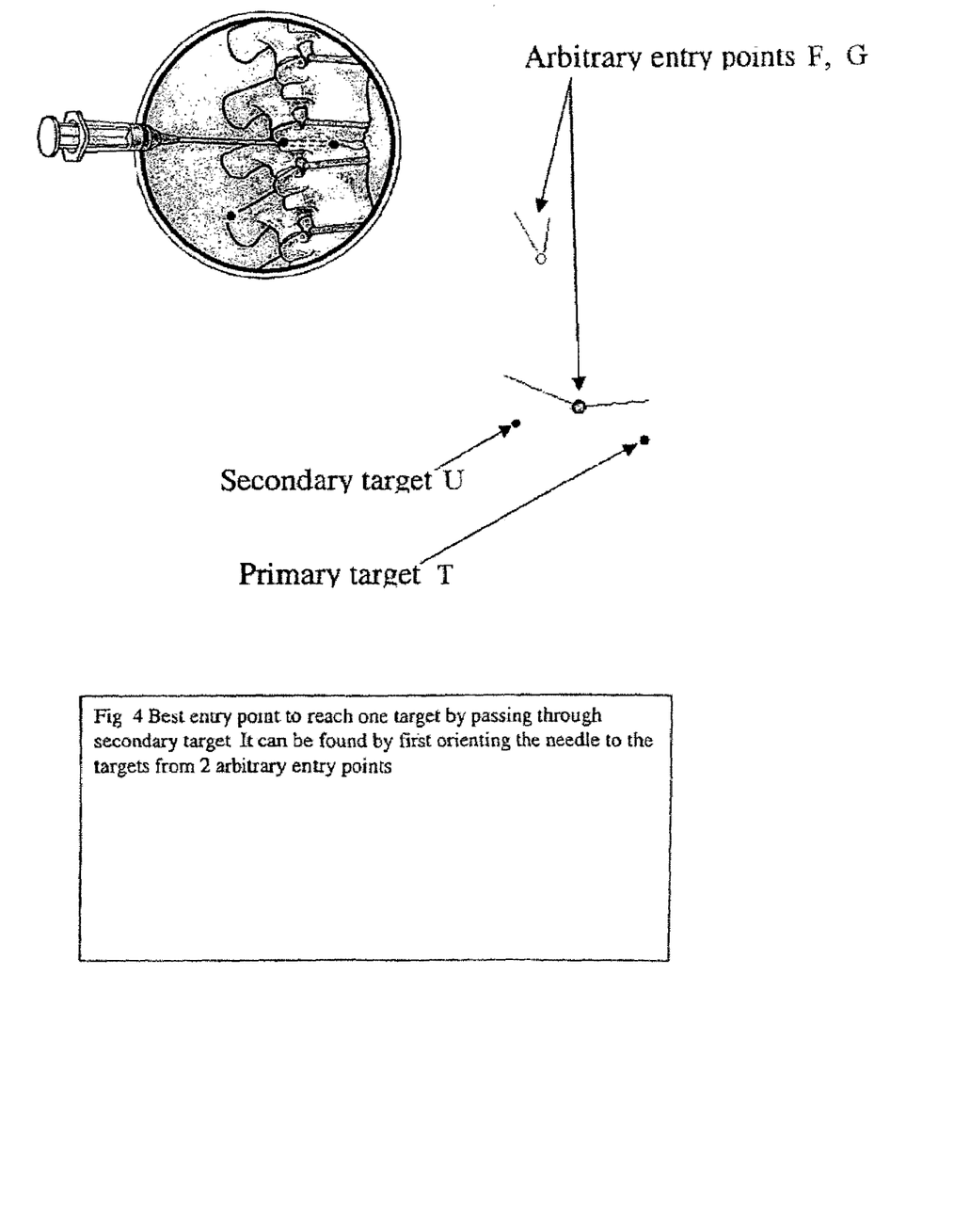
FIG. 4 shows a best entry point to reach one target by passing through a secondary target.

The approaches presented in previous sections supposes that the entry point is fixed. However, in many applications, the "optimal" entry point might not be known. An example of this are vertebroplasty procedures. Typically in those procedures the surgeon wants to reach a target point inside a vertebra and wants to use a given entry point into the vertebra. However only a highly experienced surgeon is able to determine the corresponding entry point on the skin of the patient. In this section we propose a new method to determine the entry point necessary for the needle to reach an anatomical target while passing through some given anatomical landmark. The method (illustrated by FIG. 4) is as follows:

Let T be the primary target and U the secondary target that the needle must pass through. First we choose two arbitrary entry points F and G. Then we apply the technique presented in section 1,2,3 (or any other technique that performs the 3D alignment of a needle from an entry point to a target using any imaging modality) to determine the 3D orientations of the needle necessary to reach the two targets T and U from each entry point. This gives (FT), (FU), (GT), (GU). The intersection of the planes $\Pi_{FTU}$=(FT) ∧(FU) and $\Pi_{GTU}$= (GT) ∧(GU) gives the direction (TU) that passes through both targets. The mechanical device that holds the needle can servo the needle to this direction. By lowering the servoed needle to the skin of the patient, the surgeon can find the entry point proposed by the system for reaching target T through target U.

Figure 5:
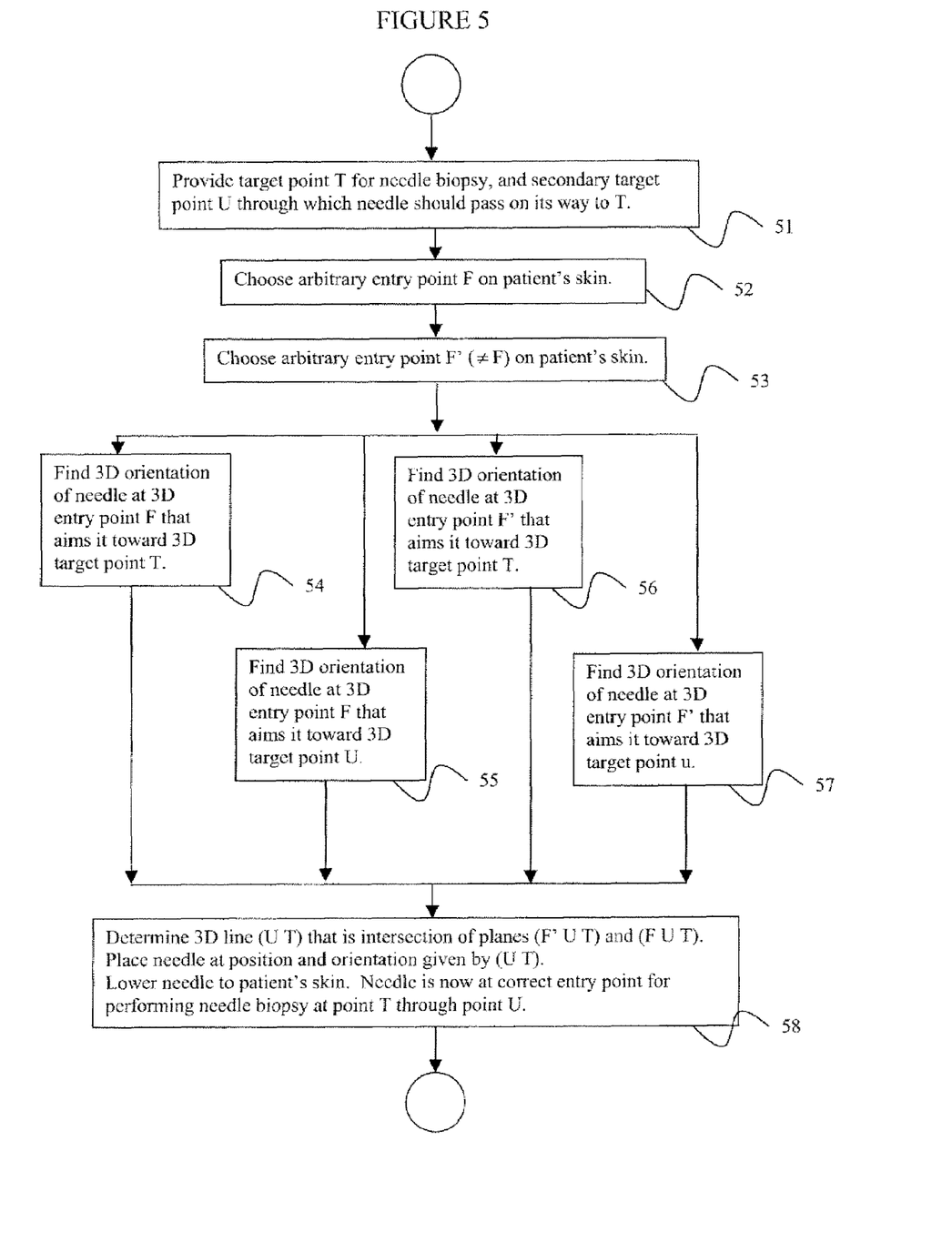
FIG. 5 shows a flow diagram or chart of a method in accordance with the invention for determining the best entry point for percutaneous procedures, given a primary target for the beiopsy and a secondary target through which the needle must pass on its way to the primary target.

In accordance with an embodiment of the invention, a primary target for biopsy and a secondary target through which a biopsy needle must pass on its way to the primary target are given. The method for determining the best entry point for a percutaneous procedure in accordance with the invention comprises steps shown in FIG. 5 for the embodiment being considered. The primary target T and secondary target U through which the needle must pass are provided at step 51. First, a first and second arbitrary entry points on a patient are selected at steps 52 and 53, respectively, the second point being different from the first point, followed by the following steps: determining at step 54 the three dimensional (3-D) orientation of the needle at the first arbitrary entry point for pointing the needle at the primary target; determining at step 55 the 3-D orientation of the needle at the first arbitrary entry point for pointing the needle at the secondary target; determining at step 56 the 3-D dimensional orientation of the needle at the second arbitrary entry point for pointing the needle at the primary target; determining at step 54 the 3-D orientation of the needle at the second arbitrary entry point for pointing the needle at the secondary target; and, at step 58, determining a 3-D line representing the intersection of a first plane containing the first arbitrary entry point, the primary target point, and the secondary target point, and a second plane containing the second arbitrary entry point, the primary target, and the secondary target point, whereby the 3-D line provides a position and orientation for the needle for performing needle biopsy of the primary target through the secondary target.

Figure 6:
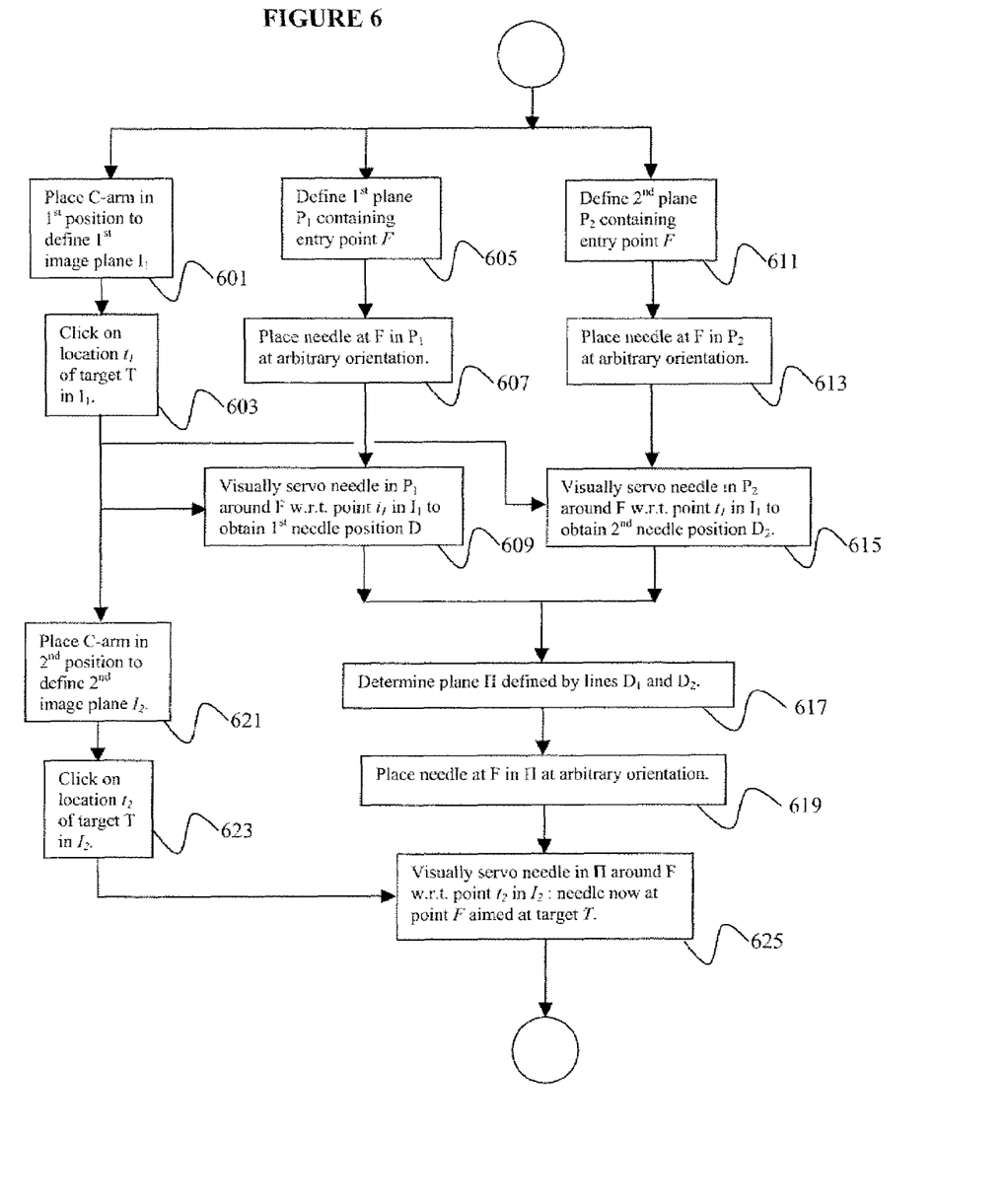
FIG. 6 shows a flow diagram or chart of a method in accordance with the invention for positioning a biopsy needle from a given entry point to a given target.

In accordance with another embodiment of the invention, a method for use in conjunction with a C-arm imaging apparatus, for positioning a biopsy needle from a given entry point F on a patient to a given target T for biopsy, comprises the steps shown in FIG. 6 for this embodiment. These comprise: positioning the C-arm in a desired first position at step 601, whereby an image formed with the C-arm in the first position is formed in a first image plane $I_1$ clicking on a location $t_1$ of the target point T in $I_1$ at step 603 and storing the location information of the given target in the first image plane; defining a first arbitrary plane $P_1$ including the given entry point F at step 605; placing the needle at the given entry point F in the first arbitrary plane at an arbitrary orientation at step 607; at step 609 visually servoing the needle in the first arbitrary plane with respect to the location $t_1$ in the first image plane to derive a first three-dimensional (3-D) needle position $D_1$; defining a second arbitrary plane $P_2$ including the given entry point F at step 611, different from the first arbitrary plane; placing the needle at the given entry point F in the second arbitrary lane at an arbitrary orientation at step 613; at step 615, visually servoing the needle in the second arbitrary plane with respect to the location $t_1$ in the image plane to derive a second three-dimensional (3-D) needle position $D_2$ determining a resulting plane defined by the first and second three-dimensional (3-D) needle positions at step 617; placing the needle at a selected point in the resulting plane at an arbitrary orientation at step 619; positioning the C-arm in a desired second position at step 621, whereby an image formed with the C-arm in the second position is formed in a second image plane $I_2$; clicking on a location $t_2$ of the target point T in $I_2$ at step 623 and storing the location information of the given target in the second image plane; and visually servoing the needle around the entry point F in the resulting plane with respect to the location $t_2$ in the second image plane at step 625, whereby the needle is at the entry point and aimed at the target.

In accordance with another embodiment of the invention for use in conjunction with a C-arm imaging apparatus, for visual servoing of a needle in a plane in a fixed number of iterations, the following are given: a given position of the C-arm being modeled on an image plane, a given target point for needle biopsy, a given entry point on a patents and a given plane within which the needle can rotate around the given entry point.

Figure 7:
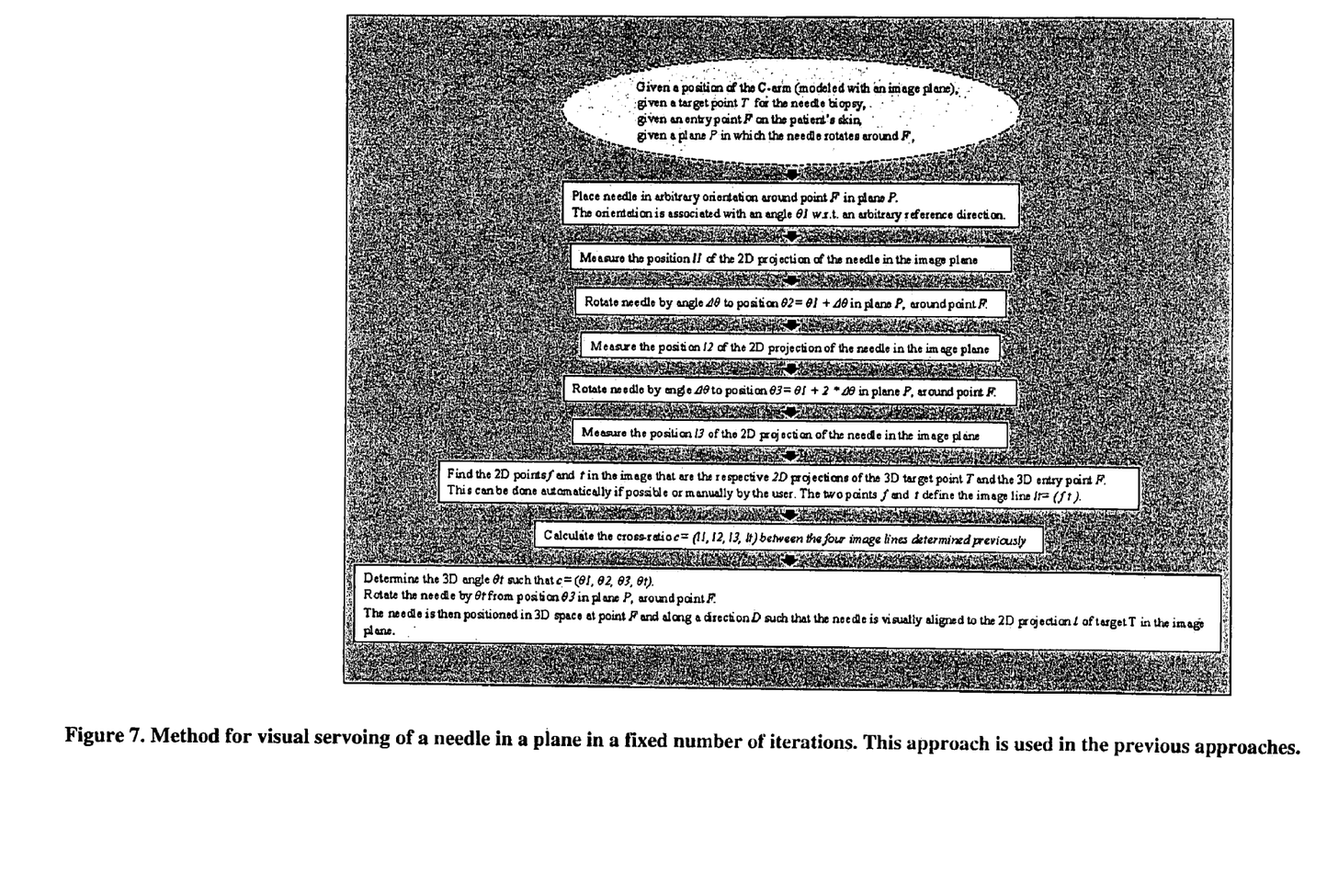
FIG. 7 shows a flow diagram or chart of a method in accordance with the invention for visual servoing of a needle in a plane in a fixed number of iterations.

The method comprises the steps shown in FIG. 7 for this embodiment. These include placing the needle in an arbitrary orientation around the given entry point, the orientation being associated with an angle θ1 with respect to an arbitrary reference direction; obtain a 2-dimensional (2-D) projection image of the needle in the image plane, measure the position 11 of the 2-D projection image; rotate the needle around the entry point by an angle Δθ to a position (θ1+Δθ) in the given plane; measure the position 12 of the 2-D projection image; rotate the needle around the entry point by an angle Δθ to a position θ3=(θ1+2*Δθ); measure the position 13 of the 2-D projection image; locate 2-D points f and t in the 2-D projection image that are the respective 2-D projections of the target point and the entry point, the points f and t defining an image line It=(ft); calculate the cross-ratio c=(11, 12, 13, It); determine a 3-D angle θt such that c=(θ1, θ2, θ3, θt); and rotate the needle around the entry point by θt from position θ3 in the given plane, whereby the needle is positioned in three dimensional space at the entry point along a direction such that the needle is visually aligned to 2-D projection image of the target in the image plane.

The step of locating 2-D points f and t is performed automatically in one embodiment and manually in another embodiment.

The use and/or incorporation of computer information processing and the storage of data is contemplated, such as the use of a programmed digital computer or a dedicated computer chip or the like.

While the present invention has been described by way of illustrative embodiments, it will be understood by one of skill in the art to which it pertains that various changes and modifications can be made without departing from the spirit of the invention. For example, where reference in the specification and in the claims is made to a biopsy needle, it will be understood that this may refer to a holder for such needle to permit alignment and manipulation of the needle itself as may be convenient. Such adjunct equipment is also described in the materials herein referenced. Such and the like modifications are intended to be within the scope of the invention as defined by the claims following.

What is claimed is:

1. A method for use in conjunction with a C-arm imaging apparatus, for positioning a biopsy needle from a given entry point on a patient to a given target for biopsy, comprising:
   positioning said C-arm in a desired first position, whereby an image formed with said C-arm in said first position is formed in a first image plane;
   storing location information of said given target in said first image plane;
   defining a first arbitrary plane including said given entry point;
   placing said needle at said given entry point;
   visually servoing said needle in said first arbitrary plane with respect to said location information in said first image plane to derive a first tree-dimensional (3-D) needle position;
   defining a second arbitrary plane including said given entry point, different from said first arbitrary plane;
   placing said needle at said given entry point;
   visually servoing said needle in said second arbitrary plane with respect to said location information in said image plane to derive a second three-dimensional (3-D) needle position;
   determining a resulting plane defined by said first and second three-dimensional (3-D) needle positions;
   placing said needle at a selected point in said resulting plane at an arbitrary orientation;
   positioning said C-arm in a desired second position, whereby an image formed with said C-arm in said second position is formed in a second image plane;
   storing location information of said given target in said second image plane; and
   visually servoing said needle around said entry point in said resulting plane with respect to said location information in said second image plane, whereby said needle is at said entry point and aimed at said target.

2. A method for use in conjunction with a C-arm imaging apparatus, for positioning a biopsy needle from a given entry point on a patient to a given target for biopsy, comprising:
   positioning said C-arm in a first position forming a first image containing said target and at least a portion of said needle;
   visually servoing said needle in a first arbitrary plane containing said entry point until a projection of the needle is aligned with said target in said first image to derive a first needle position;
   defining a second arbitrary plane including said given entry point, different from said first arbitrary plane;
   visually servoing said needle in said second arbitrary plane until a projection of said needle is visually aligned to said target in said first image to derive a second needle position, whereby a resulting plane is determined by said first and second needle positions;
   positioning said C-arm in a second position forming a second image containing said target;
   visually servoing said needle in said resulting plane until a projection of the needle is aligned with said target in said second image wherein said needle is aligned with said entry point and said target.

3. The method of claim 2, further comprising choosing a needle entry point on a patient and locating a tip of said needle at the entry point.

4. The method of claim 2, further comprising defining a projection of said target in said first image.

5. The method of claim 2, wherein said second arbitrary place is perpendicular to said first arbitrary plane.

6. The method of claim 2, further comprising defining a projection of said target in said second image.

* * * * *